(12) United States Patent
Garrison

(10) Patent No.: US 9,333,002 B2
(45) Date of Patent: May 10, 2016

(54) APPARATUS FOR PERFORMING AN ELECTROSURGICAL PROCEDURE

(75) Inventor: David M. Garrison, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1323 days.

(21) Appl. No.: 12/950,505

(22) Filed: Nov. 19, 2010

(65) Prior Publication Data
US 2012/0130367 A1    May 24, 2012

(51) Int. Cl.
*A61B 18/14* (2006.01)
*A61B 17/29* (2006.01)
*A61B 17/00* (2006.01)
*A61B 18/00* (2006.01)

(52) U.S. Cl.
CPC ............. *A61B 17/29* (2013.01); *A61B 18/1445* (2013.01); *A61B 2017/00734* (2013.01); *A61B 2017/2902* (2013.01); *A61B 2017/2934* (2013.01); *A61B 2017/2936* (2013.01); *A61B 2017/2937* (2013.01); *A61B 2018/0063* (2013.01); *A61B 2018/00589* (2013.01); *A61B 2018/00595* (2013.01); *A61B 2018/00601* (2013.01)

(58) Field of Classification Search
CPC ........... A61B 18/1442; A61B 18/1445; A61B 17/2816; A61B 17/2812; A61B 17/282; A61B 2017/2926; A61B 2017/2313; A61B 2017/2919; A61B 2017/2932; A61B 2017/2933; A61B 2017/2934
USPC ...................... 606/50–52, 205–211
See application file for complete search history.

(56) References Cited

U.S. PATENT DOCUMENTS

| | | | |
|---|---|---|---|
| 3,920,021 A * | 11/1975 | Hiltebrandt | 606/50 |
| D249,549 S | 9/1978 | Pike | |
| D263,020 S | 2/1982 | Rau, III | |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| 5,172,700 A * | 12/1992 | Bencini et al. | 600/564 |
| D343,453 S | 1/1994 | Noda | |
| D348,930 S | 7/1994 | Olson | |
| D349,341 S | 8/1994 | Lichtman et al. | |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

European Search Report for European Application No. 11189709.6 dated Jul. 12, 2012.
U.S. Appl. No. 09/387,883, filed Sep. 1, 1999, Dale F. Schmaltz.
U.S. Appl. No. 09/591,328, filed Jun. 9, 2000 Thomas P. Ryan.
U.S. Appl. No. 12/336,970, filed Dec. 17, 2008, Paul R. Sremeich.
U.S. Appl. No. 12/543,831, filed Aug. 19, 2009, Arlan J. Reschke.

(Continued)

*Primary Examiner* — Jaymi Della

(57) ABSTRACT

An endoscopic forceps is provided and includes a housing having a shaft that extends therefrom. An end effector assembly is operatively connected to a distal end of the shaft and includes a pair of pivotably coupled first and second jaw members. The jaw members are movable relative to one another. A drive mechanism includes a driving structure that is operably associated with the shaft and is operably disposed adjacent the end effector assembly. One of a driving structure guide and movable cam operably couples to the driving structure and is configured to facilitate movement of the jaw members.

13 Claims, 3 Drawing Sheets

(56) References Cited

U.S. PATENT DOCUMENTS

| | | | |
|---|---|---|---|
| 5,373,854 A * | 12/1994 | Kolozsi | 600/562 |
| D354,564 S | 1/1995 | Medema | |
| D358,887 S | 5/1995 | Feinberg | |
| 5,499,997 A * | 3/1996 | Sharpe et al. | 606/206 |
| 5,603,723 A * | 2/1997 | Aranyi et al. | 606/205 |
| D384,413 S | 9/1997 | Zlock et al. | |
| 5,797,959 A | 8/1998 | Castro et al. | |
| D402,028 S | 12/1998 | Grimm et al. | |
| D416,089 S | 11/1999 | Barton et al. | |
| D424,694 S | 5/2000 | Tetzlaff et al. | |
| D425,201 S | 5/2000 | Tetzlaff et al. | |
| D449,886 S | 10/2001 | Tetzlaff et al. | |
| 6,319,257 B1 * | 11/2001 | Carignan et al. | 606/99 |
| D454,951 S | 3/2002 | Bon | |
| D457,958 S | 5/2002 | Dycus et al. | |
| D457,959 S | 5/2002 | Tetzlaff et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,435,249 B2 | 10/2008 | Buysse et al. | |
| D582,038 S | 12/2008 | Swoyer et al. | |
| 7,494,501 B2 | 2/2009 | Ahlberg et al. | |
| 7,628,792 B2 | 12/2009 | Guerra | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 2001/0016750 A1 * | 8/2001 | Malecki et al. | 606/158 |
| 2003/0014052 A1 * | 1/2003 | Buysse et al. | 606/50 |
| 2004/0019352 A1 * | 1/2004 | Kidooka | A61B 18/1445 606/48 |
| 2006/0079890 A1 | 4/2006 | Guerra | |
| 2006/0184198 A1 * | 8/2006 | Bales et al. | 606/205 |
| 2008/0188871 A1 * | 8/2008 | Smith et al. | 606/139 |
| 2009/0062794 A1 | 3/2009 | Buysse et al. | |
| 2011/0034918 A1 | 2/2011 | Reschke | |
| 2011/0196419 A1 * | 8/2011 | Cooper | 606/206 |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 02617 | 12/2005 |
| DE | 20 2007 00916 | 10/2007 |
| DE | 20 2007 00931 | 10/2007 |
| DE | 19738457 | 1/2009 |
| EP | 1159926 | 12/2001 |
| EP | 1568330 | 8/2005 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 10-24051 | 1/1998 |
| JP | 11-070124 | 5/1998 |
| JP | 2000-102545 | 9/1998 |
| JP | 11-169381 | 6/1999 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/15614 | 3/2001 |
| WO | WO 01/54604 | 8/2001 |
| WO | WO 05/110264 | 11/2005 |
| WO | WO 2009067649 | 5/2009 |

OTHER PUBLICATIONS

U.S. Appl. No. 12/548,031, filed Aug. 26, 2009, Peter M. Mueller.
U.S. Appl. No. 12/548,534, filed Aug. 27, 2009, Thomas J. Gerhardt.
U.S. Appl. No. 12/548,566, filed Aug. 27, 2009, John J. Kappus.
U.S. Appl. No. 12/551,944, Sep. 1, 2009, Sean T. Dycus.
U.S. Appl. No. 12/553,509, filed Sep. 3, 2009, Paul R. Romero.
U.S. Appl. No. 12/556,025, filed Sep. 9, 2009, Arlen J. Reschke.
U.S. Appl. No. 12/556,407, filed Sep. 9, 2009, Kim V. Brandt.
U.S. Appl. No. 12/556,427, filed Sep. 9, 2009, Peter M. Mueller.
U.S. Appl. No. 12/556,796, filed Sep. 10, 2009, Jennifer S. Harper.
U.S. Appl. No. 12/562,281, filed Sep. 18, 2009, Patrick L. Dumbauld.
U.S. Appl. No. 12/565,281, filed Sep. 23, 2009, William J. Dickhans.
U.S. Appl. No. 12/568,199, filed Sep. 28, 2009, Kim V. Brandt.
U.S. Appl. No. 12/568,282, filed Sep. 28, 2009, Kim V. Brandt.
U.S. Appl. No. 12/568,838, filed Sep. 29, 2009, Kenlyn S. Bonn.
U.S. Appl. No. 12/569,395, filed Sep. 29, 2009, Weng-Kai K. Lee.
U.S. Appl. No. 12/569,710, filed Sep. 29, 2009, Dylan R. Kingsley.
U.S. Appl. No. 12/574,001, filed Oct. 6, 2009, Duane E. Kerr.
U.S. Appl. No. 12/574,292, filed Oct. 6, 2009, Duane E. Kerr.
U.S. Appl. No. 12/576,380, filed Oct. 9, 2009, Wayne Siebrecht.
U.S. Appl. No. 12/597,213, filed Oct. 23, 2009, Ryan Artale.
U.S. Appl. No. 12/607,191, filed Oct. 28, 2009, William H. Nau, Jr.
U.S. Appl. No. 12/619,100, filed Nov. 16, 2009, Jennifer S. Harper.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Homer.
U.S. Appl. No. 12/769,444, filed Apr. 28, 2010, Glenn A. Norner.
U.S. Appl. No. 12/770,369, filed Apr. 29, 2010, Glenn A. Horner.
U.S. Appl. No. 12/770,380, filed Apr. 29, 2010, Glenn A. Homer.
U.S. Appl. No. 12/770,387, filed Apr. 29, 2010, Glenn A. Homer.
U.S. Appl. No. 12/773,526, filed May 4, 2010, Duane E. Kerr.
U.S. Appl. No. 12/773,644, filed May 4, 2010, Thomas J. Gerhardt.

(56) References Cited

OTHER PUBLICATIONS

U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/950,791, filed Nov. 19, 2010, Patrick L. Dumbauld.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967, British Medical Journal Feb. 6, 1976, Vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; Vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.

(56) References Cited

OTHER PUBLICATIONS

Rothenberg et al. "Use of the LigaSure Vessel Sealing System in Minimally Invasive Surgery in Children" Int'L Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'L Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'L Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

APPARATUS FOR PERFORMING AN ELECTROSURGICAL PROCEDURE

BACKGROUND

1. Technical Field

The present disclosure relates to an apparatus for performing an electrosurgical procedure. More particularly, the present disclosure relates to an electrosurgical apparatus including an end effector assembly having a pair of jaw members that provide a mechanical advantage at the end effector.

2. Description of Related Art

Electrosurgical instruments, e.g., electrosurgical forceps (open or closed type), are well known in the medical arts and typically include a housing, a handle assembly, a shaft and an end effector assembly attached to a distal end of the shaft. The end effector includes jaw members configured to manipulate tissue (e.g., grasp and seal tissue). Typically, the electrosurgical forceps utilizes both mechanical clamping action and electrical energy to effect hemostasis by heating the tissue and blood vessels to coagulate, cauterize, seal, cut, desiccate, and/or fulgurate tissue. Typically, one or more driving mechanisms, e.g., a drive assembly including a drive element, is utilized to cooperate with one or more components operatively associated with the end effector to impart movement to one or both of the jaw members.

To facilitate moving the jaw members from an open position for grasping tissue to a closed position for clamping tissue (or vice versa) such that a consistent, uniform tissue effect (e.g., tissue seal) is achieved, one or more types of suitable devices may be operably associated with the electrosurgical forceps. For example, in some instances, one or more cam members, e.g., a cam pin, may operably couple to the drive element, e.g., a drive rod, wire, cable, etc., and operably couple to a cam slot that is operably associated with one or both of the jaw members. Typically, the cam slots are operably disposed on proximal end of the jaw members. In certain instances, to facilitate movement of the jaw members, the proximal ends of the jaw members are configured to extend outside of the shaft profile. In this extended position, the proximal ends of the jaw members are commonly referred to as "flags."

In certain instances, the shaft may bend or deform during the course of an electrosurgical procedure. For example, under certain circumstances, a clinician may intentionally bend or articulate the shaft to gain a desired mechanical advantage at the surgical site. Or, under certain circumstances, the surgical environment may cause unintentional or unwanted bending or flexing of the shaft, such as, for example, in the instance where the shaft is a component of a catheter-based electrosurgical forceps. More particularly, shafts associated with catheter-based electrosurgical forceps are typically designed to function with relatively small jaw members, e.g., jaw members that are configured to pass through openings that are 3 mm or less in diameter. Accordingly, the shaft and operative components associated therewith, e.g., a drive rod, are proportioned appropriately. That is, the shaft and drive rod are relatively small.

As can be appreciated, when the shaft is bent or deformed (either intentionally or unintentionally) the frictional losses associated with "flags" extending through the shaft profile may be transferred to one of the drive rod, drive element, and/or a spring operably associated with the drive assembly, which, in turn, may diminish, impede and/or prevent effective transfer of the desired closure force that is needed at the jaw members. Moreover, the frictional losses may also lessen the operative life of the spring, which, in turn, ultimately lessens the operative life of the electrosurgical instrument.

SUMMARY

The present disclosure provides an endoscopic forceps. The endoscopic forceps includes a housing having a shaft that extends therefrom and defines a longitudinal axis therethrough. An end effector assembly is operatively connected to a distal end of the shaft and includes a pair of first and second jaw members. The first and second jaw members are pivotably coupled to one another. The first and second jaw members are movable relative to one another from an open position, wherein the first and second jaw members are disposed in spaced relation relative to one another, to a clamping position, wherein the first and second jaw members cooperate to grasp tissue therebetween. A drive mechanism includes a driving structure with a bifurcated distal end having two substantially resilient legs. A driving structure guide is operably associated with the shaft and is operably disposed adjacent the end effector assembly. The driving structure guide includes at least two grooves each configured to receive respective ones of the two legs of the bifurcated distal end.

The present disclosure provides endoscopic forceps. The endoscopic forceps includes a housing having a shaft that extends therefrom and defines a longitudinal axis therethrough. An end effector assembly is operatively connected to a distal end of the shaft and includes a pair of first and second jaw members. The first and second jaw members are pivotably coupled to one another via a central pivot pin. The first and second jaw members are movable relative to one another from an open position, wherein the first and second jaw members are disposed in spaced relation relative to one another, to a clamping position, wherein the first and second jaw members cooperate to grasp tissue therebetween. A drive mechanism is operably associated with the housing and includes a driving structure. A movable cam operably disposed adjacent the end effector includes two or more cam slots thereon. The two or more cam slots are in operative communication with respective cam followers that are operably coupled to respective ones of the first and second jaw members. The respective cam followers angled offset from the pivot pin such that a closure force in the range from about 3 kg/cm$^2$ to about 16 kg/cm$^2$ is present at the first and second jaw members when the first and second jaw members are in the clamping position.

BRIEF DESCRIPTION OF THE DRAWING

Various embodiments of the present disclosure are described hereinbelow with references to the drawings, wherein.

DETAILED DESCRIPTION

Figure 1:
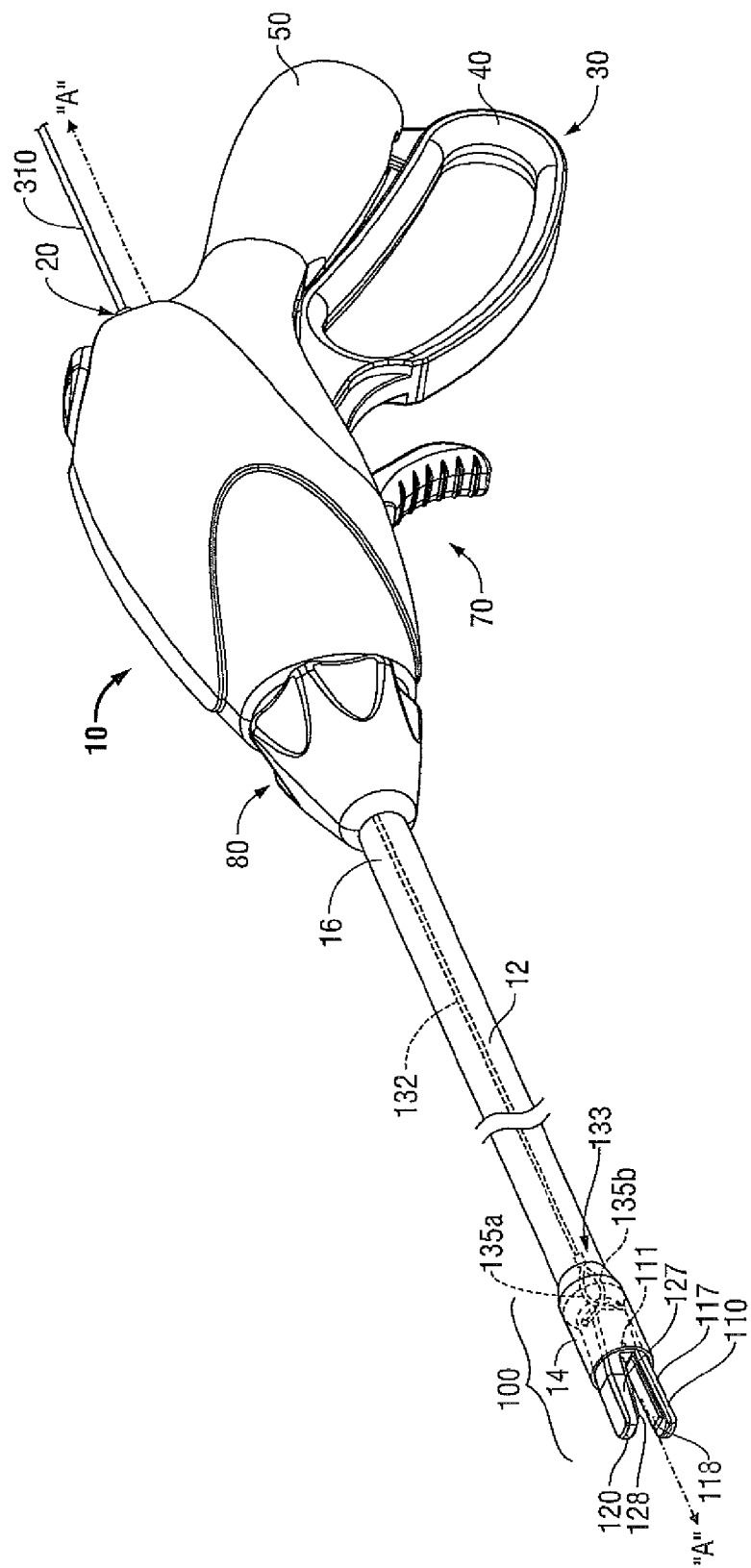
FIG. 1 is a side, perspective view of an endoscopic bipolar forceps showing an end effector assembly including jaw members according to an embodiment of the present disclosure.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, will refer to an end that is closer to the user, while the term "distal" will refer to an end that is farther from the user.

Figure 2:
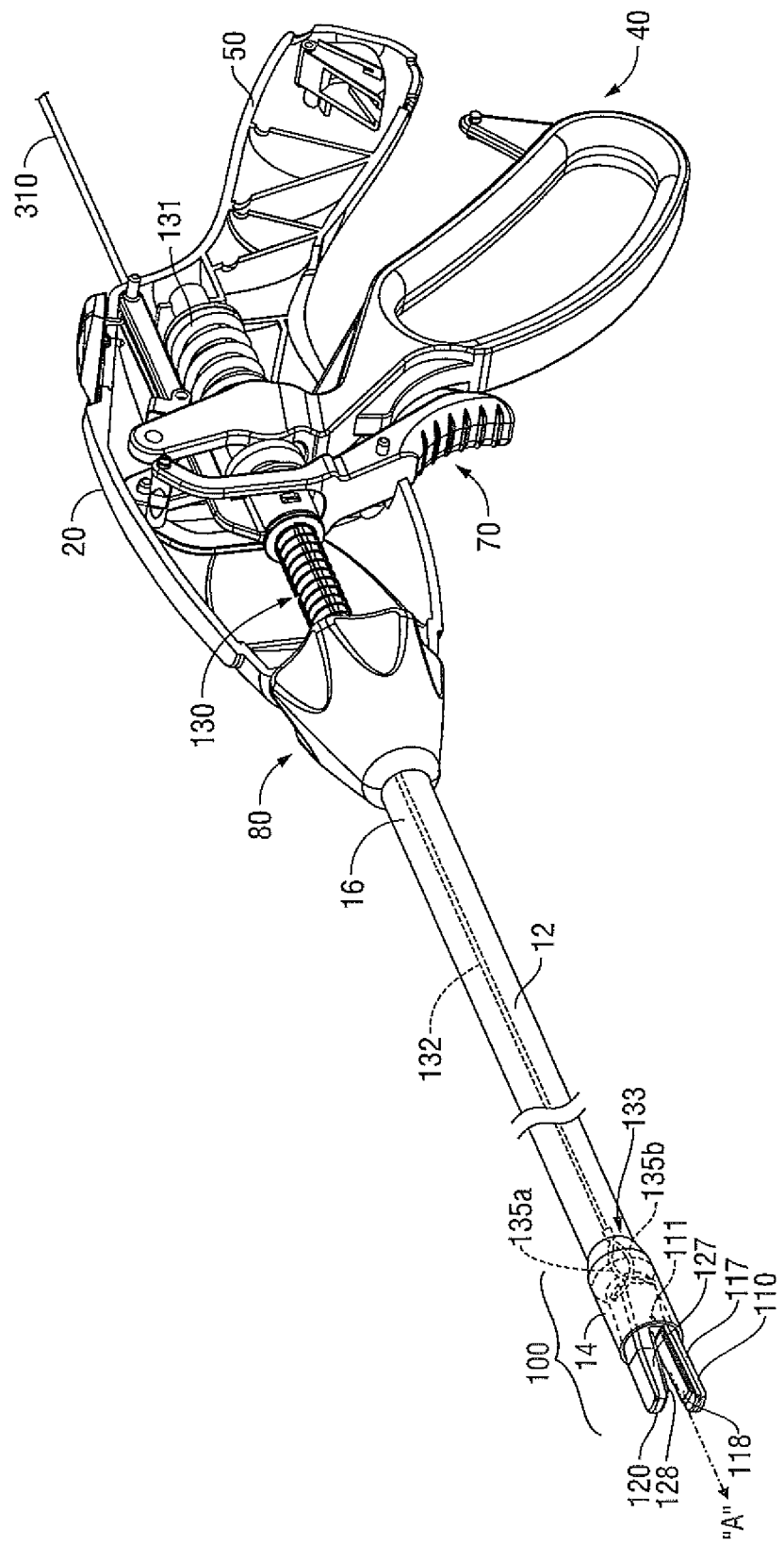
FIG. 2 is a side, perspective view of the endoscopic bipolar forceps depicted in FIG. 1 illustrating internal components associated with a handle assembly associated with the endoscopic bipolar forceps.

With reference to FIGS. 1 and 2, an illustrative embodiment of an electrosurgical apparatus, e.g., a bipolar forceps 10 (forceps 10) is shown. Forceps 10 is operatively and selectively coupled to an electrosurgical generator (not shown) for performing an electrosurgical procedure. As noted above, an electrosurgical procedure may include sealing, cutting, cauterizing, coagulating, desiccating, and fulgurating tissue all of which may employ RF energy. The electrosurgical generator may be configured for monopolar and/or bipolar modes of operation and may include or be in operative communication with a system that may include one or more processors in operative communication with one or more control modules (not shown) that are executable on the processor. The control module may be configured to instruct one or more modules to transmit electrosurgical energy, which may be in the form of a wave or signal/pulse, via one or more cables (e.g., an electrosurgical cable 310) to the forceps 10. However, in certain embodiments, the forceps 10 may be battery powered. In this instance, the forceps 10 is not configured to communicate with either an electrosurgical generator and/or a system.

Forceps 10 is shown configured for use with various electrosurgical procedures and generally includes a housing 20, electrosurgical cable 310 that connects the forceps 10 to the electrosurgical generator, a rotating assembly 80 and a trigger assembly 70. For a more detailed description of the rotating assembly 80, trigger assembly 70, and electrosurgical cable 310 (including line-feed configurations and/or connections), reference is made to commonly-owned U.S. patent application Ser. No. 11/595,194 filed on Nov. 9, 2006 now U.S. Patent Publication No. 2007/0173814.

With continued reference to FIGS. 1 and 2, forceps 10 includes a shaft 12 that has a distal end 14 that is configured to mechanically engage an end effector assembly 100 operably associated with the forceps 10 and a proximal end 16 that mechanically engages the housing 20.

Figure 3:
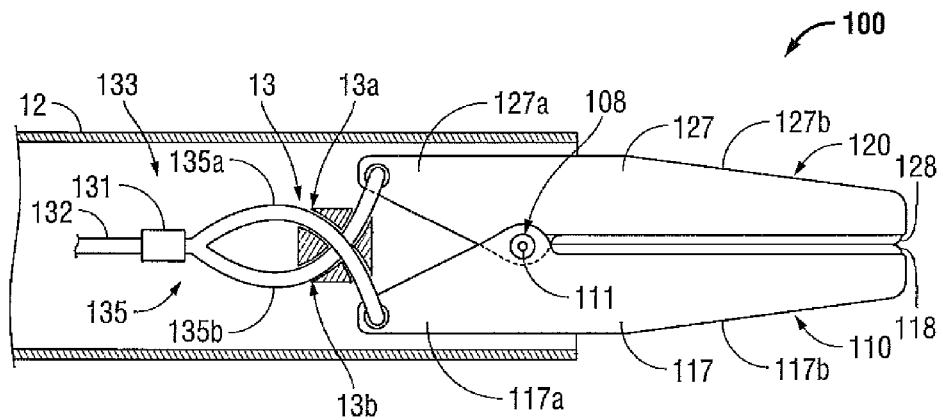
FIG. 3 is a schematic view of the jaw members depicted in FIGS. 1 and 2 illustrating a distal end of a driving structure operably coupled to the jaw members.

One or more driving structures or guides are operably associated with the shaft 12. More particularly, as best seen in FIG. 3, a drive wire guide 13 (guide 13) of suitable proportion is operably disposed adjacent the distal end 14 of the shaft 12, as best seen in FIG. 3. Guide 13 may be made from any suitable material including, but not limited to, plastic, metal, metal alloy, etc. Guide 13 is operably coupled to an internal frame of the shaft 12 by one or more suitable coupling methods. In the illustrated embodiment, guide 13 is monolithically formed, e.g., molding, stamping, machining, etc., with the shaft 12.

Guide 13 is in operative communication with a drive mechanism 130 (FIG. 2). Specifically, guide 13 includes a multi-grooved (or multi-slotted) configuration that is configured to receive a driving structure 133 (or operative component associated therewith) that is operably associated with the drive mechanism 130 (FIGS. 1 and 2). More specifically, guide 13 includes a first groove 13a that is configured to receive a leg or branch 135a of a bifurcated distal end 135 that is operably coupled driving structure 133. Likewise, a second groove 13b is configured to receive a leg or branch 135b of the bifurcated distal end 135.

Each of the first and second grooves 13a and 13b includes a generally arcuate configuration that extends along a respective length thereof. The arcuate configuration of the grooves 13a and 13b facilitates movement of the respective legs 135a and 135b therein. Moreover, the arcuate configuration of the grooves 13a and 13b allows a greater length of the legs 135a and 135b to be positioned within the grooves 13a and 13b for a given area within the shaft 12.

With reference again to FIGS. 1 and 2, handle assembly 30 includes a fixed handle 50 and movable handle 40. In one particular embodiment, fixed handle 50 is integrally associated with housing 20. Movable handle 40 is movable relative to fixed handle 50 for effecting movement of one or more components, e.g., driving structure 133, operably associated with drive mechanism 130 (FIG. 2). Handle assembly 30 including movable handle 40 may be configured such that proximal movement of the movable handle 40 "pulls" the driving structure 133, which, in turn, imparts movement of one or both of a pair of jaw members 110 and 120 from a normally closed or clamping position (FIGS. 2 and 3) to an open position (FIG. 1). Alternatively, handle assembly 30 including movable handle 40 and drive mechanism 130 may be configured such that proximal movement of the movable handle 40 "pushes" the driving structure 133, which, in turn, imparts movement of the jaw members 110 and 120.

Drive mechanism 130 is in operative communication with movable handle 40 (see FIGS. 1 and 2) for imparting movement of both or, in some instances, one of the jaw members 110, 120 of end effector assembly 100. More particularly, one or more suitable mechanical interfaces, e.g., a linkage interface, gear interface, or combination thereof operably couples the movable handle 40 to the drive mechanism 130. In the embodiment illustrated in FIGS. 1-3, proximal movement of the movable handle 40 moves the jaw members 110 and 120 away from each other from the normally closed position to the clamping position.

Driving structure 133 is configured such that proximal movement thereof causes the jaw members 110 and 120 to move from the clamping position (FIGS. 2 and 3) to the open position (FIG. 1) and vice versa. To this end, driving structure 133 may be any suitable driving structure including but not limited to a wire, rod, cable, resilient band, etc. In the illustrated embodiment, driving structure 133 is a drive wire 132 of suitable configuration (FIGS. 1-4).

Drive wire 132 includes a proximal end (not explicitly shown) that is in operative communication with the movable handle 40.

The bifurcated distal end 135 operably couples to the drive wire 132 and includes legs 135a and 135b that are configured to translate within the guide 13 (see FIG. 3, for example). Drive wire 132 is configured such that the drive wire 132 including the bifurcated distal end 135 does not tend to "buckle" or "kink" when the drive wire 132 is moved proximally and/or distally within the shaft 12 and through the guide 13.

The bifurcated distal end 135 including the legs 135a and 135b may be a wire, a band, a cable or the like. In the illustrated embodiment, the distal end 135 including the legs 135a and 135b is a substantially flexible wire of suitable dimensions. In some embodiments, the bifurcated distal end 135 may be a combination of two or more materials and/or structure. For example, and in one particular embodiment, the bifurcated distal end 135 may include a proximal wire portion that operably couples to a pair of legs 135a and 135b that are flexible bands. Other configurations are contemplated.

Leg 135a is movable within the first groove 13a. Likewise, leg 135b is movable within the second groove 13b. To facilitate independent movement of the legs 135a and 135b within the respective first and second grooves 13a and 13b of the guide 13, the legs 135a and 135b are positioned therein in a criss-crossed manner and/or pattern, as best seen in FIG. 3. More particularly, the legs 135a and 135b "cross-over" one another at a medial point within the guide 13. Positioning the legs 135a and 135b in this manner within the guide 13 allows that legs 135a and 135b to move in concert with and independent of one another within the respective first and second grooves 13a and 13b while allowing the legs 135a and 135b to concomitantly move the jaw members 110 and 120 from the clamping to open position and vice versa.

A distal end of leg 135a is operably coupled (by one or more suitable coupling methods, e.g., indent/detent configuration) to a proximal end 117a of a jaw housing 117. Similarly, a distal end of leg 135b is operably coupled (by one or more suitable coupling methods, e.g., indent/detent configuration) to a proximal end 127a of a jaw housing 127.

To facilitate movement of the legs 135a and 135b within the respective first and second grooves 13a and 13b, the bifurcated distal end 135 including legs 135a and 135b and/or guide 13 including first and second grooves 13a and 13b may be coated with one or more types of lubricious materials, e.g., PTFE.

One or more suitable coupling devices operably couples the bifurcated distal end 135 to the drive wire 132. In embodiment illustrated in FIG. 3, a coupler 131 is utilized to couple the distal end 135 to the drive wire 132. The coupler 131 includes proximal and distal threaded ends (not explicitly shown) that threadably couple to corresponding threaded ends associated with the distal end 135 and drive wire 132. As can be appreciated, other coupling methods are contemplated, e.g., the drive wire 132 may have the bifurcated distal end 135 monolithically formed therewith.

End effector assembly 100 is illustrated operably disposed at the distal end 14 of the shaft 12 (FIGS. 1-3). End effector assembly 100 includes opposing jaw members 110 and 120 that mutually cooperate to grasp, seal and, in some cases, divide large tubular vessels and large vascular tissues. As noted above, in the illustrated embodiment, jaw members 110 and 120 are movable relative to each other. Jaw members 110, 120 are operatively and pivotably coupled via a central pivot pin 111 to each other and located adjacent the distal end 14 of shaft 12. Respective electrically conductive seal plates 118 and 128 are operably supported on and secured to respective distal ends 117b and 127b of jaw housings 117 and 127 of the jaw members 110 and 120, respectively. Jaw members 110 and 120 including respective jaw housings 117 and 127, and operative components associated therewith, may be formed from any suitable material, including but not limited to metal, metal alloys, plastic, plastic composites, and so forth.

Jaw housing 127 and 117 of the respective jaw members 120 and 110 are substantially identical to each other. In view thereof, the operative features of jaw housing 127 are described in detail, and only those features that are unique to jaw housing 117 are described hereinafter.

With reference to FIG. 3, an embodiment of jaw housing 127 is illustrated. Jaw housing 127 includes a distal end 127b that is configured to operably support seal plate 128 and a proximal end 127a that operably couples to the distal end 14 of shaft 12. Proximal end 127a includes a generally angled configuration (FIG. 3) and is configured to move, e.g., pivot, within the shaft 12 from the closed or clamping position to the open position (see also FIG. 1 in combination with FIG. 2). Pivot pin 111 couples the first and second jaw members 110 and 120, respectively (FIGS. 1-3) for pivotal movement relative to one another.

The jaw members 110 and 120 may be coupled to each other via any suitable coupling methods. In the illustrated embodiment, an opening 108 is defined in and extends through the each of the jaw housings 117 and 127 and is configured to receive pivot pin 111. Opening 108 is shown engaged with pivot pin 111 and, as such, is not explicitly shown.

In an assembled configuration, pivot pin 111 is positioned within the opening 108 associated with each of the jaw members 110 and 120, respectively. Once assembled, the jaw members 120 and/or jaw member 110 may be pivotably supported at the distal end 14 of the shaft 12 by known methods, such as, for example, by the method described in commonly-owned U.S. Pat. No. 7,597,693 to Garrison.

To facilitate pivotable movement of the jaw members 110 and 120, in the assembled configuration, the guide 13 is offset (or otherwise spaced) from the proximal ends 117a and 127a of respective jaw members 110 and 120. Accordingly, the guide 13 does not contact the proximal ends 117a and 127a and, thus, does not interfere or impede movement of the jaw members 110 and 120 when the jaw members are moved from the clamping to the open position.

In use, jaw members 110 and 120 are, initially, in the clamping position (see FIGS. 2 and 3). Movable handle 40 is moved proximally (FIG. 1), which, in turn, causes the drive wire 132 to move proximally. Proximal movement of the drive wire 132 moves the bifurcated distal end 135 including the legs 135a and 135b proximally within the respective first and second grooves 13a and 13b. Proximal movement of the legs 135a and 135b causes the respective jaw members 110 and 120 to move away from one another to the open position, see FIG. 1, for example. Subsequently, tissue is positioned between the jaw members 110 and 120. Once tissue is positioned between the jaw members 110 and 120, movable handle is released and the jaw members 110 and 120 move toward one another and back to the clamping position with tissue disposed therebetween. In the clamping position closure force in the range from about 3 kg/cm$^2$ to about 16 kg/cm$^2$ may be present at the jaw members 110 and 120. Thereafter, tissue is electrosurgically treated, e.g., tissue is sealed. In one embodiment, a closure force in the range of 3 kg/cm$^2$ to about 16 kg/cm$^2$ is used to obtain desired tissue seal characteristics, i.e., is used to provide a uniform and consistent seal across the tissue.

The unique configuration of the bifurcated distal end 135 and guide 13 improves the opening and closing angles typically associated with known forceps jaw designs. More particularly, the unique configuration of the guide 13 facilitates turning and routing the drive wire 132 therethrough. Moreover, the unique configuration of the guide 13 including the bifurcated distal end 135 having the non-coupled criss-crossed configuration of the legs 135a and 135b eliminates the need of having the proximal ends 117a and 127a ("flags") extend past the profile of the shaft 12.

From the foregoing and with reference to the various figure drawings, those skilled in the art will appreciate that certain modifications can also be made to the present disclosure without departing from the scope of the same. For example, it is contemplated that in certain instances one or more resilient members, e.g., compression spring (not shown), may be operably associated with or coupled to either bifurcated distal end 135 and/or one or both of the jaw members 110 and 120. In this instance, the spring may be configured to provide a clamping force or seal force between the jaw members 110 and 120 when the jaw members 110 and 120 are in the clamping position.

It is contemplated that in certain embodiments, the legs 135a and 135b and the respective first and second grooves 13a and 13b may function as or include a ratchet and pawl system. In this instance, each of the legs 135a and 135b and the respective first and second grooves 13a and 13b may be configured to lock the jaw members 110 and 120 in one or more positions, e.g., the clamping position.

Figure 4:
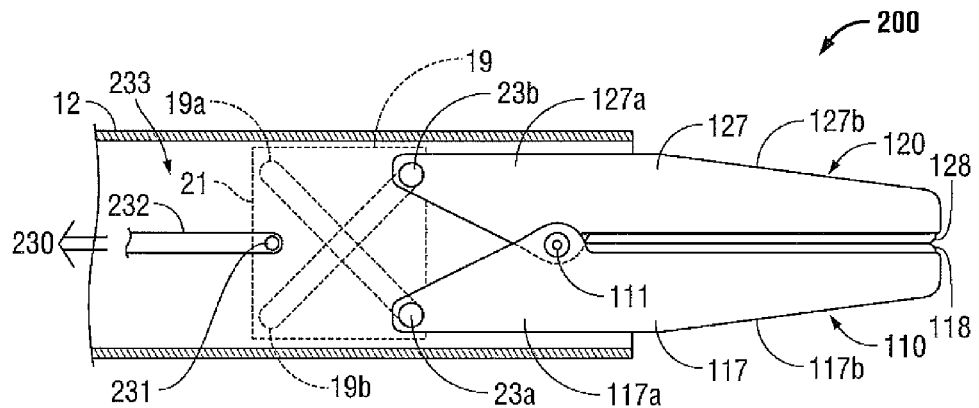
FIG. 4 is a schematic view illustrating a distal end of a driving structure operably coupled to the jaw members of the end effector depicted in FIGS. 1 and 2 according to another embodiment of the present disclosure.

With reference to FIG. 4, an end effector 200 that is suitable for use with the forceps 10 is shown. It should be noted that end effector 200 is substantially identical to end effector 100 described above. In view thereof, and so as not to obscure the present disclosure with redundant information, only the operative components associated with end effector 200 will be described hereinafter.

A drive mechanism 230 includes a drive structure 233. Drive structure 233 may be any suitable drive structure 233 including but not limited to a substantially flexible rod, cable, band or the like. In the illustrated embodiment, drive structure 233 is a substantially flexible drive rod 232. Drive mechanism 150 including drive rod 232 is configured such that proximal movement of the movable handle 40 causes distal movement of the drive rod 232, which, in turn, imparts movement of the jaw member 110 and 120 from the clamping position (FIG. 4) to the open position, see FIG. 1, for example.

Unlike end effector 100 that is operably associated with a guide 13, end effector 200 is operably associated with a movable cam 19 (cam 19), see FIG. 4. Cam 19 may be made from any suitable material including but not limited to the materials previously described above with respect to guide 13, e.g., plastic. Cam 19 may include any suitable shape. In the embodiment illustrated in FIG. 4, cam 19 includes a generally rectangular configuration. A proximal end 21 of the cam 19 is operably coupled to a distal end of a drive rod 232 by one or more suitable coupling methods, e.g., soldering, brazing, welding, adhesive, rivet, pin, etc. In the illustrated embodiment, proximal end 21 operably couples to the distal end of a drive rod 232 by way of a rivet 231.

Two or more cam slots 19a and 19b of suitable proportion are operably disposed on the cam 19 (FIG. 4). To facilitate opening and closing the jaw members 110 and 120, cam slots 19a and 19b are disposed in different planes and in a generally criss-crossed manner so that the cam pins 23a and 23b do not intersect each other during opening and closing of the jaw members 110 and 120.

Continuing with reference to FIG. 4, cam slot 19a operably couples to a cam follower, e.g., a cam pin 23a, that is operably disposed on jaw member 110 at a proximal end 117a thereof. Similarly, Cam slot 19b operably couples to a cam follower, e.g., a cam pin 23b that is operably disposed on jaw member 120 at a proximal end 127a thereof. The cam pins 23a and 23b are offset from the pivot pin 111 at a predetermined angle such that, in one embodiment, a closure force in the range from about 3 kg/cm$^2$ to about 16 kg/cm$^2$ is present at the jaw members 110 and 120 when the first and second jaw members are in the clamping position. In the illustrated embodiment, the cam pins are offset from the pivot pin 111 at an angle (that ranges from about 25° to about 65° and a distance to provide desired forces and mechanical advantages for a specific application. Offsetting the cam pins 23a and 23b at desirable angles with respect to the pivot pin 111 facilitates movement of the proximal ends 117a and 127a within the limited area at the distal end 14 of the shaft 12.

To facilitate movement of the cam pins 23a and 23b within the respective cam slots 19a and 19b, the cam pins 23a and 23b and/or cam slots 19a and 19b may be coated with one or more types of lubricious materials, e.g., PTFE.

In use, jaw members 110 and 120 are, initially, in the clamping position (see FIGS. 2 and 4). Movable handle 40 is moved proximally (FIG. 1), which, in turn, causes the drive rod 232 and the cam 19 including cam slots 19a and 19b to move distally. Distal movement of the cam 19 including the cam slots 19a and 19b cams the respective cam pins 23a and 23b causing the respective jaw members 110 and 120 to move away from one another to the open position, see FIG. 1, for example. Subsequently, tissue is positioned between the jaw members 110 and 120. Once tissue is positioned between the jaw members 110 and 120, movable handle is released (or moved proximally depending on the specific configuration of the Movable handle 40) and the jaw members 110 and 120 move toward one another and back to the clamping position with tissue disposed therebetween. In certain instances, the jaw members 110 and 120 may be spring biased in either an open or closed configuration. In the clamping position closure force in the range from about 3 kg/cm$^2$ to about 16 kg/cm$^2$ is present at the jaw members 110 and 120. Thereafter, tissue is electrosurgically treated, e.g., tissue is sealed. In one embodiment, a closure force in the range of 3 kg/cm$^2$ to about 16 kg/cm$^2$ is used to obtain desired tissue seal characteristics, i.e., is used to provide a uniform and consistent seal across the tissue.

The movable cam 19 including cam slots 19a and 19b improves the opening and closing angles typically associated with known forceps jaw designs. More particularly, the unique crisscrossed configuration of the cam slots 19a and 19b facilitates camming the cam pins 23a and 23b therein. Moreover, the unique configuration of the crisscrossed configuration of the cam slots 19a and 19b eliminates the need of having the proximal ends 117a and 127a ("flags") extend past the profile of the shaft 12. Further, the unique configuration of the crisscrossed configuration allows the cam slots to be formed as a separate piece, from a separate process or with a separate material. As can be appreciated, this may change cam slot shapes, e.g., curvature and angles, and resulting mechanical advantages.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. An endoscopic forceps, comprising:
a housing having a shaft that extends therefrom and defines a longitudinal axis therethrough;
an end effector assembly operatively connected to a distal end of the shaft and including first and second jaw members pivotably coupled to one another, at least one of the first and second jaw members movable relative to the other of the first and second jaw members from an open position, wherein the first and second jaw members are disposed in spaced relation relative to one another, to a clamping position, wherein the first and second jaw members cooperate to grasp tissue therebetween;

a drive mechanism including a single driving structure with a bifurcated distal end having two substantially resilient legs, wherein longitudinal translation of the single driving structure with respect to the shaft results in the first and second jaw members moving from the open position to the clamping position, the drive mechanism generating a closure force in a range from about 3kg/cm$^2$ to about 16 kg/cm$^2$ between the first and second jaw members;

a movable handle operably associated with the housing and configured to actuate the drive mechanism when the movable handle is moved proximally such that the first and second jaw members move from the clamping position to the open position; and a driving structure guide operably associated with the shaft and operably disposed adjacent the end effector assembly, the driving structure guide includes at least two grooves each configured to receive a respective one of the two substantially resilient legs of the bifurcated distal end, wherein the driving structure guide is fixed from movement with regard to the shaft, and wherein a first groove of the at least two grooves guides the respective one of the two substantially resilient legs of the bifurcated distal end along a curved path with respect to the longitudinal axis.

2. The endoscopic forceps according to claim 1, wherein each of the at least two grooves includes a generally arcuate configuration with respect to the longitudinal axis, wherein the generally arcuate configuration extends along a respective length of each of the at least two grooves.

3. The endoscopic forceps according to claim 1, wherein the single driving structure is selected from the group consisting of a rod, a cable, a wire, and a band.

4. The endoscopic forceps according to claim 3, wherein the single driving structure is a wire.

5. The endoscopic forceps according to claim 4, wherein the bifurcated distal end is operably coupled to the wire via a threaded couple.

6. The endoscopic forceps according to claim 5, wherein each of a distal end of the wire and the bifurcated distal end is threaded and configured to threadably connect to the threaded couple.

7. The endoscopic forceps according to claim 1, wherein the substantially resilient legs of the bifurcated distal end are disposed in the driving structure guide in a non-coupled, criss-crossed manner.

8. The endoscopic forceps according to claim 1, wherein the bifurcated distal end including the two substantially resilient legs is selected from the group consisting of a cable, a wire, and a band.

9. The endoscopic forceps according to claim 1, wherein the bifurcated distal end including the two substantially resilient legs is configured to move proximally within the driving structure guide in response to proximal movement of the movable handle, such that the first and second jaw members move from the clamping position to the open position.

10. The endoscopic forceps according to claim 1, wherein the two substantially resilient legs are longitudinally translatable with respect to the driving structure guide, and wherein the two substantially resilient legs are longitudinally translatable at least partially through the driving structure guide.

11. The endoscopic forceps according to claim 1, wherein a proximal opening of the first groove is laterally offset from a distal opening of the first groove with respect to the longitudinal axis.

12. The endoscopic forceps according to claim 1, wherein a proximal opening of the first groove is on a first lateral side of the longitudinal axis, and a distal opening of the first groove is on a second lateral side of the longitudinal axis.

13. An endoscopic forceps, comprising:

a housing having a shaft that extends therefrom and defines a longitudinal axis therethrough;

an end effector assembly operatively connected to a distal end of the shaft and including first and second jaw members pivotably coupled to one another, at least one of the first and second jaw members movable relative to the other of the first and second jaw members from an open position, wherein the first and second jaw members are disposed in spaced relation relative to one another, to a clamping position, wherein the first and second jaw members cooperate to grasp tissue therebetween;

a drive mechanism including two legs, wherein longitudinal translation of the driving structure with respect to the shaft results in the first and second jaw members moving from the open position to the clamping position; and a driving structure guide operably associated with the shaft and operably disposed adjacent the end effector assembly, the driving structure guide includes at least two grooves each configured to receive a respective one of the two legs of the drive mechanism, and wherein a first groove of the at least two grooves guides a respective one of the two legs along a curved path with respect to the longitudinal axis.

* * * * *